United States Patent [19]

Bendix et al.

[11] Patent Number: 4,960,866

[45] Date of Patent: Oct. 2, 1990

[54] CATALYST-FREE RESORBABLE HOMOPOLYMERS AND COPOLYMERS

[75] Inventors: Dieter Bendix; Gunther Entenmann, both of Ingelheim am Rhein, Fed. Rep. of Germany

[73] Assignee: Boehringer Ingelheim Zentrale, Ingelheim am Rhein, Fed. Rep. of Germany

[21] Appl. No.: 301,200

[22] Filed: Jan. 24, 1989

Related U.S. Application Data

[63] Continuation of Ser. No. 128,855, Dec. 4, 1987, abandoned.

[30] Foreign Application Priority Data

Dec. 6, 1986 [DE] Fed. Rep. of Germany ....... 3641692

[51] Int. Cl.$^5$ .............................................. C08G 63/74
[52] U.S. Cl. .................................. 528/499; 528/354; 528/355
[58] Field of Search ........................ 528/354, 355, 499

[56] References Cited

U.S. PATENT DOCUMENTS

| | | | |
|---|---|---|---|
| 3,297,033 | 1/1967 | Schmitt et al. | 528/357 X |
| 3,442,871 | 5/1969 | Schmitt et al. | 528/357 |
| 3,560,450 | 2/1971 | Curotti | 528/357 X |
| 4,237,265 | 12/1980 | Eliasson et al. | 528/499 X |
| 4,273,920 | 6/1981 | Nevin | 528/354 X |
| 4,464,526 | 8/1984 | Mueller | 528/355 X |
| 4,595,713 | 6/1986 | St. John | 528/354 X |
| 4,677,191 | 6/1987 | Tanaka et al. | 528/354 X |
| 4,683,288 | 7/1987 | Tanaka et al. | 528/354 X |
| 4,728,721 | 3/1988 | Yamamoto et al. | 528/354 X |

*Primary Examiner*—Earl Nielsen
*Attorney, Agent, or Firm*—Alan R. Stempel; Mary-Ellen M. Timbers; Daniel Reitenbach

[57] ABSTRACT

The invention relates to resorbable homopolymers and copolymers which are substantially free from polymerization catalysts and processes for preparing them.

3 Claims, No Drawings

CATALYST-FREE RESORBABLE HOMOPOLYMERS AND COPOLYMERS

This is a continuation of application Ser. No. 128,855, filed Dec. 4, 1987 now abandoned.

The invention relates to catalyst-free resorbable homopolymers and copolymers and processes for preparing them.

In recent years, interest in the use of resorbable polyesters has increased sharply; for example in the field of surgery, for use as stitching material or clamps, in osteosynthesis or as active substance carriers with a delayed controlled release of active substance. As is already known from numerous publications, the major advantage of resorbable polyesters, particularly those based on lactic or glycolic acid, is the fact that they are broken down completely in human or animal tissue to form compounds which occur naturally in the body. These breakdown products pass into the normal biochemical metabolism and are eventually metabolized to form water and carbon dioxide. A disadvantage of the use of resorbable homopolymers and copolymers is the catalyst content. When the polymers are resorbed, a finite quantity of catalyst is left behind in the tissues, since the catalyst cannot be broken down here. Consequently irritation may occur in the tissues, and depending on the catalyst, there is even a possibility of poisoning. Furthermore, the catalyst remaining in the homopolymer or copolymer may also lead to transesterification or even to the uncontrolled breakdown of the polymer and thus, for example, result in an unpredictable rate of release of an active substance from a delayed-release form. Uncontrolled release may also lead to fracture of an implant in the case of osteosynthesis.

Catalyst-free copolymers based on lactic and glycolic acid are known. By direct condensation of lactic and glycolic acid or by co-condensation of these two compounds it is possible to obtain low molecular weight polymers, preferably with a molecular weight of from 2000 to 4000. Attempts at achieving high molecular weights by direct condensation have, however, resulted in the cleavage of lactide or glycolide. A possible cause of this is the fact that in order to separate off the water of condensation resulting from the polyester formation, which is, in any case, only present in traces, the pressure and temperature have to be adjusted so that the reaction conditions approximate to those of lactide or glycolide synthesis, so that there is at least some depolymerization.

The use of strongly acidic ion exchangers for preparing a catalyst-free copolymer from glycolide and lactide is known from European Pat. No. 26 599. Using the process described therein, it is possible to produce copolymers with a molecular weight of from 6000 up to a maximum of 35000.

It is also known from European Patent Application No. 171 907 to prepare copolymers of lactic and glycolic acid with molecular weights of up to about 20700 by "dehydration polycondensation".

As has been found in recent years, the use of resorbable polyesters is very strongly linked to the chemical and physical properties of these polymers. By varying the composition of the comonomers, the method of polymerization and the choice of suitable catalysts, it was possible to prepare polymers which were suited to their intended use (e.g. stitching material, resorbable or partially resorbable osteosynthetic material, galenic preparations), but these polymers still contain finite quantities of catalyst.

Hitherto, the only catalyst-free copolymers of lactide and glycolide known from the prior art are those having an average molecular weight of up to 35000, at most. However, this significantly restricts their use, since in many cases it is essential to use polymers with higher molecular weights.

The invention provides resorbable homopolymers and copolymers which are substantially free from catalyst. Suitable polymers in accordance with the invention are those which are soluble in an organic solvent, optionally after suitable pretreatment, e.g. tempering. Homo- and co-polymers based on hydroxycarboxylic acids, such as polymers of glycolide, lactide, methylglycolide, dimethylglycolide, polymethylglycolide, diethylglycolide, dibutylglycolide, caprolactone, valerolactone, decalactone, propiolactone, butyrolactone and pivalolactone; polymers based on trioxane, 1,3-dioxan-2-one or 1,4-dioxane, substituted 1,3-dioxan-2-one or 1,4-dioxanone, trimethylenecarbonate, ethylenecarbonate and propylenecarbonate are preferred.

Other suitable comonomers include the following compounds:

lactic acid, glycolic acid, pentaerythritol, sorbitol, adonitol, xylitol, fructose, epichlorohydrin, isopropylmorpholine, isopropylmethylmorpholinedione, $\beta$-propiolic acid, tetramethyl glycolide, $\beta$-butyrolactone, q-butyrolactone, pivalolactone, a-hydroxybutyric acid, a-hydroxyisobutyric acid, a-hydroxyvaleric acid, a-hydroxyisovaleric acid, a-hydroxycaproic acid, a-hydroxyisocaproic acid, a-hydroxy-a-ethylbutyric acid, a-hydroxy-$\beta$-methylvaleric acid, a-hydroxyheptanoic acid, a-hydroxyoctanoic acid, a-hydroxydecanoic acid, a-hydroxytetradecanoic acid and a-hydroxystearic acid.

Catalyst-free homopolymers of lactide, catalyst-free copolymers of different lactides and catalyst-free copolymers of lactides and glycolide with inherent viscosities of between 0.1 and 10 dl/g are particularly preferred.

The lactide used may be l-, d-, meso- or dl-lactide or mixtures thereof. With copolymers of glycolide and lactide, the solubility of the particular copolymer is strongly dependent on the glycolide content.

Homopolymers of l-lactide with an inherent viscosity of 0.1 to 10 dl/g are also preferred. From the inherent viscosity, the corresponding average molecular weight is calculated at 2000 to 1.4 million (see. W. Dittrich and R. C. Schulz, Angew. Makro. Chem., 15 (1971) 109–126).

Also preferred are homopolymers of dl-lactide with an inherent viscosity of 0.1 to at least 5 dl/g, corresponding to average molecular weights of 2000 to at least 1.5 million, calculated from the inherent viscosity by approximation of the Staudinger index according to Solomon and Ciuta (see. J. Appl. Polym. Sci., 6.24 (1962) 683–6) and putting into the Mark-Houwink equation the parameters $K=6.06\times10^{-4}$ and $a=0.64$ (see. J. Rak, J. L. Ford, Ch. Rostron and V. Walther, Pharm. Acta Helv., 60, 5–6 (1985) 162–9).

Copolymers of l-lactide and glycolide are also preferred having inherent viscosities of from greater than 1.4 to at least 4.5 dl/g (wherein, on account of the fact that the copolymers containing a high proportion of glycolide begin to be insoluble, the glycolide content generally does not exceed 50%). Using the method described above and the Mark-Houwink parameters $K=5.45\times10^{-4}$ and $a=0.73$ (see. S. Gogolewski and A.

J. Pennings, J. Appl. Polym. Sci., 28, 1045–61) average molecular weights of from 50000 to at least 250000 are calculated. (As used in this specification, the term "average molecular weight" refers to weight average molecular weight.)

Other preferred copolymers are those of dl-lactide and glycolide with inherent viscosities of at least 1.5 dl/g, corresponding to average molecular weight of at least 55000, calculated using the above Mark-Houwink parameters for copolymers; also copolymers of epsilon-caprolactone with l- or dl-lactide and glycolide and inherent viscosities of up to at least 4 dl/g; also poly(l-lactide-co-dl-lactide) in the ratio 9:1, poly(l-lactide-co-glycolide) in the ratio 7:3, poly(dl-lactide-co-glycolide) in the ratio 3:1, poly(dl-lactide-co-glycolide) in the ratio 1:1, poly(dl-lactide-co-glycolide) in the ratio 45:55.

For example, homopolymers and copolymers of lactic and glycolic acid are preferably prepared by ring-opening polymerization of the cyclic diesters of lactic and glycolic acids, namely the lactide and glycolide. Owing to the chirality of lactic acid, the optically active l- and d-lactides and the optically inactive meso-lactide and the racemate (dl-lactide) ma be included in the ring-opening polymerisation.

The conditions of this polymerization are known. A variety of compounds mostly containing polyvalent metal ions are cited in the literature as suitable catalysts for polymerization. Tin(II) or zinc compounds are preferably used. Of the tin compounds, tin(II) di(2-ethylhexanoate) (tin octoate) is preferred.

The homopolymers are prepared in solution or emulsion or in a melt. The copolymers of any desired composition may be prepared in emulsion owing to the different reactivities of the two comonomers but are preferably prepared by bulk polymerization in a melt. During the polymerization, the desired molecular weight and the corresponding molecular weight distribution may be achieved by varying the reaction parameters of temperature, time and catalyst concentration and by adding one or more co-catalysts.

The catalyst-containing polymers prepared by known methods are dissolved in a suitable organic solvent or in a mixture of various organic solvents which must not be fully miscible with water. Generally, the concentration of the dissolved polymer in the solvent should not exceed 10% since otherwise the solution would become too viscous and satisfactory processing would no longer be guaranteed. A content of between 0.5 and 4.0%, particularly between 0.5 and 2.0%, is preferred. The organic solution of the homopolymer or copolymer is then brought into intimate contact with water, an aqueous solution of an inorganic acid, a water-soluble organic acid or a water-soluble complexing agent. After a contact time sufficient to allow the catalyst to go into the aqueous phase, the phases are separated and the organic phase containing the catalyst-free polymer is dried. Finally, the polymer is recovered from the organic phase by known methods.

Suitable solvents are those which dissolve the homopolymer or copolymer but are immiscible or only slightly miscible with water or at least form a 2-phase system in a specific mixing ratio. Preferred solvents are halogenated hydrocarbons such as methylene chloride or chloroform. The solubility of the polymers depends substantially on their composition and can be determined by simple tests. In some cases, mixtures of solvents may also prove particularly suitable. In cases of polymers of limited solubility, e.g. copolymers containing a high proportion of glycolide, pretreatment, for example by heating or irradiation of the polymer, is advantageous in order to increase its solubility. Suitable inorganic acids include for example hydrochloric, sulphuric or phosphoric acid, but monofunctional or polyfunctional water-soluble organic acids such as acetic or citric acid may also be used. A suitable complexing agent is EDTA (ethylenediamine tetraacetate) in the form of the free acid or the sodium salt. The concentration of the acids or complexing agents used is not critical. Conveniently, a 0.1 to 5% aqueous solution, preferably 0.1 to 1% aqueous solution, is used. If strongly concentrated acids are used, however, it is impossible to rule out the possibility that the inherent viscosity of the polymer will decrease. Processes for establishing intimate contact between the two immiscible phases are sufficiently well known. On a laboratory scale, simply stirring or shaking once or several times has proved completely adequate. On an industrial scale, contact between the two immiscible phases is appropriately established by uniflow or counterflow extraction. Such processes are part of the prior art and need not be explained in detail here. Extraction is continued or repeated until no further metal or metal ions can be detected in the homopolymer or copolymer by the method of atomic absorption or any other suitable analytical method.

After the phase separation, the organic phase is dried and the homopolymer or copolymer is recovered, for example by a suitable method of precipitation, and, after being dried, is characterized by measurement of the inherent viscosity. Suitable methods of precipitation include the addition of an adequate quantity of precipitation agent, preferably a low-boiling petroleum ether fraction. The inherent viscosity is measured in a suitable solvent, e.g. chloroform or hexafluoroisopropanol, at temperatures of 25° or 30° C. The term "inherent viscosity" is taken to mean the quotient of the natural logarithm of relative viscosity and the concentration of the measured solution, given in [g/dl]. Using equations known from the literature, it is possible to calculate from the inherent viscosity the Staudinger index (intrinsic viscosity) and, if the corresponding parameters are known, using the Mark-Houwink equation, the average molecular weight. The molecular weight distribution and the polydispersity of the polymers and copolymers is preferably measured by exclusion chromatography such as high pressure size exclusion chromatography (HPSEC) in chloroform, methylene chloride, dioxan, THF or HFIP. Calibration is carried out by known methods against narrowly distributed poly(styrene) standards. It was established that the process according to the invention for removing the catalyst did not adversely affect the properties of the polymer or copolymer (e.g. expressed by the inherent viscosity).

Owing to the fact the polymers according to the invention are virtually free from polymerization catalyst, they are particularly suitable for the manufacture of objects which can be resorbed in human or animal bodies. These include, in particular, surgical stitching material, objects for use in osteosynthesis and carriers for pharmaceutical active substances. The latter may, for example, be in the form of tablets or capsules but may also take the form of implantable or injectable delayed-release forms.

The following are some typical products for medical use which may advantageously be made from catalyst-free polymers.

Catalyst-free products made from restorable polymers:

| 1. Solid products, compression moulded or machined: |
| --- |
| Orthopaedic pins, clamps, screws and plates, clips (e.g. for vena cava), staples, hooks, buttons and press-studs, bone replacements (e.g. jaw prostheses), needles, non-permanent intrauterine inserts (spermicidal), temporary drainage or exploration tubes or capillaries, surgical instruments, blood vessel implants or supports, vertebrae, extracorporeal tubes for kidney and heart-lung machines, slowly disintegrating ion exchange resin, slowly disintegrating products which release active substances (pills, pellets), reinforced bone pins, needles etc., implantable pellets, sticks, films and other shaped objects charged with pharmaceutical compositions for the controlled release of active substance. |
| 2. Fibre products, knitted or woven, including velour |
| burn bandages, fracture pads, absorbent paper or swabs, medicinal dressings, items used in plastic surgery, gauze, tissue, cloth, felt or sponge for haemostasis, gauze bandages, dental fillings, stitching material including ligatures. Arterial transplants or replacements, bandages for the surface of the skin, burn dressings (combined with other polymer films). |
| 3. Powdered products produced by spray drying, grinding, precipitation or microencapsulation. Injectable or implantable powder charged with drugs for the controlled and delayed release of the active substance. Microporous shaped objects, films, powders and granules for charging with active substances. |
| 4. Miscellaneous |
| Flakes or powders for treating burns or abrasions, foam as an absorbable prosthesis, substitutes for wire in splints, film spray for prosthetic elements and for the treatment of wounds. |

EXAMPLES

EXAMPLE 1

Comparative Example 16 g of poly(dl-lactide-co-glycolide) in a molar ratio of 1:1, with a tin content of 550 ppm and an inherent viscosity of 0.37 dl/g in chloroform at 25° C. are dissolved in 80 ml of acetone at boiling temperature, filtered and then precipitated in water. The copolymer is removed by suction filtering, washed with cold water and dried in a vacuum or circulating air drier. The tin content of the sample is determined by atomic absorption spectrometry and the inherent viscosity is measured in chloroform at 25° C.

Yield: 89.8% of the starting quantity
Inherent viscosity: 0.40 dl/g
Tin content: 415 ppm

EXAMPLE 2

100 ml batches of a 1% chloroform solution of a poly(l-lactide) with an inherent viscosity of 1.47 dl/g and a tin content of 254 ppm are stirred with 100 ml of 0.1N hydrochloric acid for various lengths of time.

After phase separation and drying of the organic phase with sodium sulphate the poly(l-lactide) is reprecipitated by the addition of petroleum ether with a boiling range of 40°-60° C. and dried in a vacuum drying cupboard at about 40° C. until a constant weight is achieved.

The tin content of each sample is determined by atomic absorption.

| Stirring time [minutes] | tin content [ppm] |
| --- | --- |
| 0 | 254 |
| 5 | 29 |
| 15 | 2 |

EXAMPLE 3

100 ml batches of a 1% chloroform solution of a poly(l-lactide) with an inherent viscosity of 1.47 dl/g in chloroform at 25° C. and with a tin content of 254 ppm are stirred once, twice and three times each time with 100 ml of a 0.1N hydrochloric acid for 5 minutes. The phases are separated, the aqueous phases are discarded and the organic phases are dried with sodium sulphate. The poly(l-lactide) is reprecipitated by the addition of petroleum ether with a boiling range of 40°-60° C. and dried in a vacuum drying cuboard at about 40° C. until a constant weight is achieved. The yield in each case is 85% of the starting amount.

The tin content of each sample is determined by atomic absorption.

| Stirring time [number of times] | tin content [ppm] |
| --- | --- |
| 0 | 254 |
| 1 | 29 |
| 2 | 2 |
| 3 | 2 |

EXAMPLE 4

100 ml of a 1% solution of a poly(l-lactide) in chloroform with an inherent viscosity of 1.47 dl/g and a tin content of 254 ppm are stirred with 100 ml of water, or of a 1% aqueous solution of an organic acid, an inorganic acid or a complexing agent for 15 minutes. The mixture is left to stand for 10 minutes and then the phases are separated. The aqueous phase is discarded. After phase separation and drying of the organic phase with sodium sulphate, the poly(l-lactide) is reprecipitated by the addition of petroleum ether with a boiling range of 40°-60° C. and dried in a vacuum drying cupboard at about 40° C. until a constant weight is achieved.

| Aqueous solution | Yield [% of material used] | Sn content [ppm] |
| --- | --- | --- |
| water | 90 | 2 |
| sulphuric acid | 94 | 2 |
| hydrochloric acid | 91 | 2 |
| acetic acid | 92 | 2 |
| phosphoric acid | 88 | 2 |

| Aqueous solution | Yield [% of material used] | Sn content [ppm] |
| --- | --- | --- |
| citric acid | 90 | 2 |
| EDTA | 95 | 2 |

EXAMPLE 5

100 ml batches of a 1% solution in chloroform of a poly(dl-lactide-co-glycolide) with a tin content of 550 ppm are stirred for 15 minutes with 100 ml of a 1% hydrochloric acid solution.

After phase separation and drying of the organic phase with sodium sulphate the copolymer is re-precipitated and dried in a vacuum drying cupboard at about 40° C. until a constant weight is achieved.

| Molar Ratio | Yield [% of material used] | Sn content [ppm] |
| --- | --- | --- |
| 50:50 | 99 | 2 |
| 75:25 | 96 | 2 |

What is claimed is:

1. A process for producing catalyst-free resorbable homopolymers or copolymers comprising the steps of: (a) dissolving a catalyst-containing polymer in an organic solvent which is immiscible with water, (b) bringing the thus dissolved polymer into intimate contact with water or with an aqueous phase which contains an inorganic acid, a water-soluble organic acid or a water-soluble complexing agent, (c) separating the organic phase from the aqueous phase, and (d) isolating the polymer from the organic phase.

2. The process as claimed in claim 1, characterized in that the acid or the complexing agent is present in the aqueous phase in a concentration of from about 0.1 to 5%.

3. The process as claimed in claims 1 or 2, characterized in that the concentration of the dissolved polymer in the organic solvent does not exceed about 10%.

* * * * *